(12) United States Patent
Kang et al.

(10) Patent No.: US 8,257,269 B2
(45) Date of Patent: Sep. 4, 2012

(54) APPARATUS FOR ANALYSING PULSE USING ARRAY OF PRESSURE SENSORS

(75) Inventors: Hee-Jung Kang, Ansan-si (KR); Young-Sang Kwon, Ansan-si (KR)

(73) Assignee: Daeyo Medi Co., Ltd., Ansan-Si (KR)

( * ) Notice: Subject to any disclaimer, the term of this patent is extended or adjusted under 35 U.S.C. 154(b) by 855 days.

(21) Appl. No.: 12/305,859

(22) PCT Filed: Jun. 21, 2006

(86) PCT No.: PCT/KR2006/002396
§ 371 (c)(1), (2), (4) Date: Dec. 19, 2008

(87) PCT Pub. No.: WO2007/148841
PCT Pub. Date: Dec. 27, 2007

(65) Prior Publication Data
US 2010/0168592 A1 Jul. 1, 2010

(51) Int. Cl.
*A61B 5/02* (2006.01)
(52) U.S. Cl. ........................................ 600/502; 600/500
(58) Field of Classification Search ........................ None
See application file for complete search history.

(56) References Cited

U.S. PATENT DOCUMENTS

| 5,170,796 | A | 12/1992 | Kobayashi |
| 6,607,492 | B2 | 8/2003 | Ogura |
| 6,932,772 | B2 | 8/2005 | Kan |
| 2003/0212335 | A1* | 11/2003 | Huang ........................ 600/500 |
| 2010/0168592 | A1* | 7/2010 | Kang et al. .................... 600/502 |

* cited by examiner

*Primary Examiner* — Shanon A Foley
(74) *Attorney, Agent, or Firm* — Sherr & Vaughn, PLLC

(57) ABSTRACT

Disclosed is an apparatus for analyzing pulse using an array of pressure sensors comprising: an array of pressure sensors that measures the pulse data with a plurality of piezoresistive pressure sensors; a moving part that moves the array of pressure sensors; a controller that controls the moving part, so that the array of pressure sensors can be positioned at the pulse diagnosis site, and analyzes the pulse data measured by the array of pressure sensors; and a display that displays the pulse profile analyzed by the controller. Since both the applied pressure and the pulse pressure can be measured simultaneously using the piezoresistive pressure sensors, various pulse diagnosis techniques can be applied and since pulse length, pulse thickness, etc. can be displayed in four dimensions, softness or roughness of the pulse and other pulse information can be conveyed visually.

6 Claims, 6 Drawing Sheets

[Fig. 1]
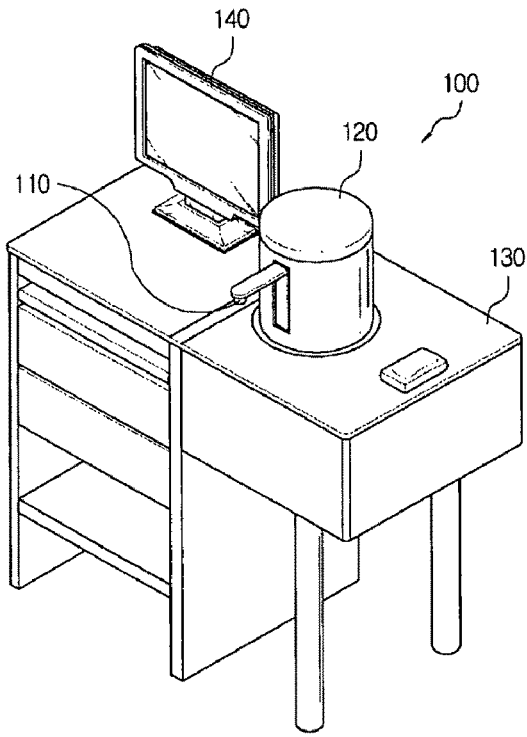
[Fig. 2]
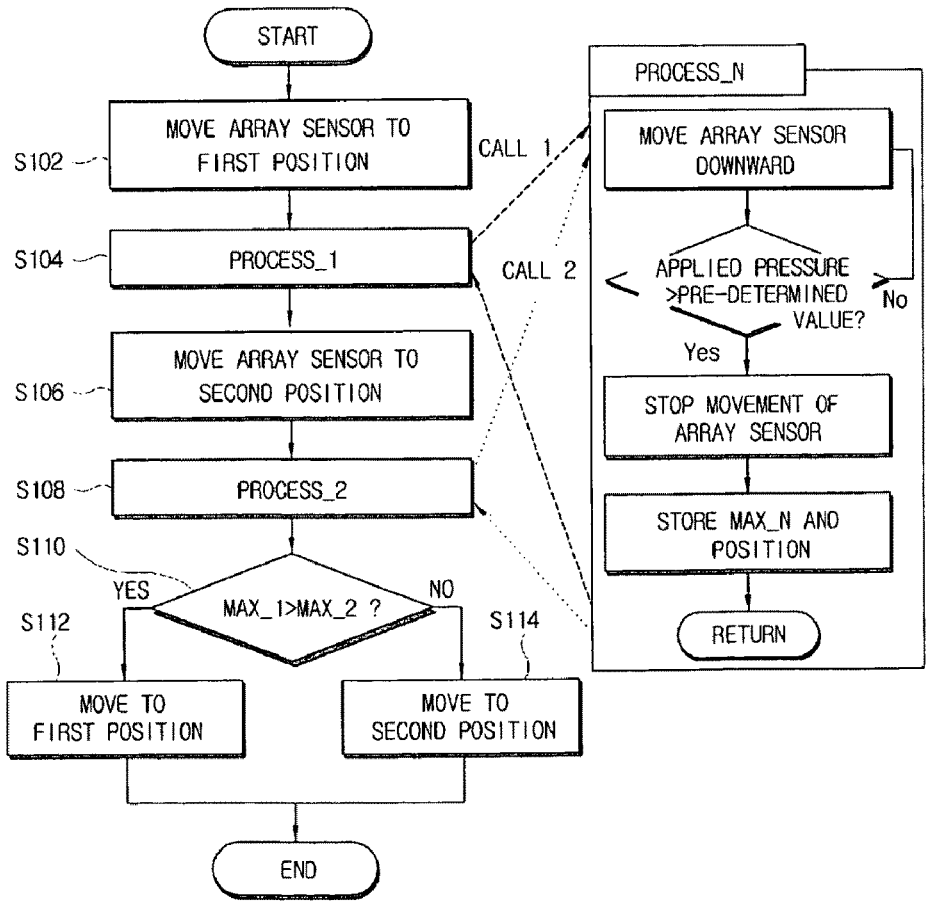

[Fig. 3]
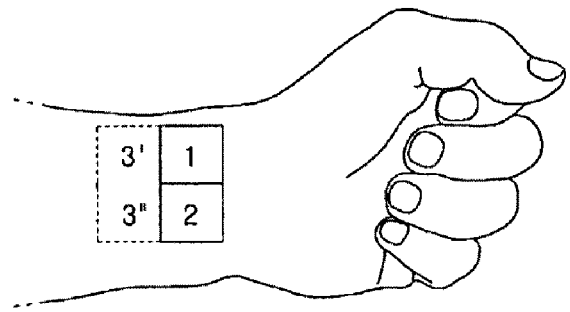
[Fig. 4]
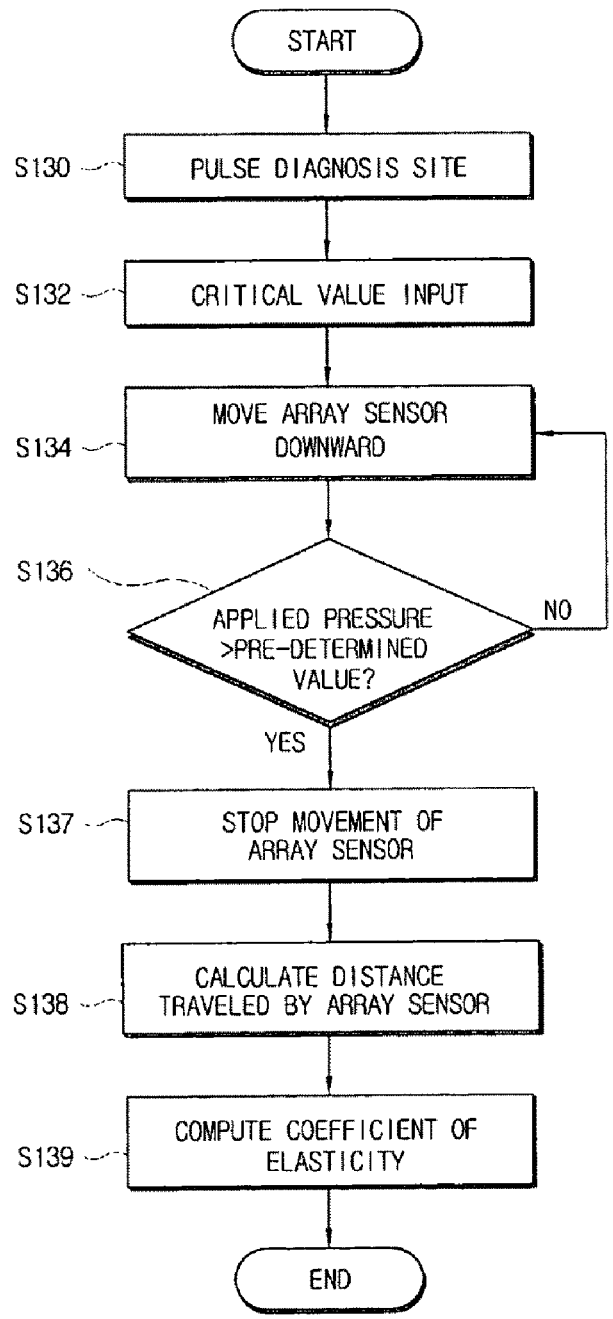

[Fig. 5]
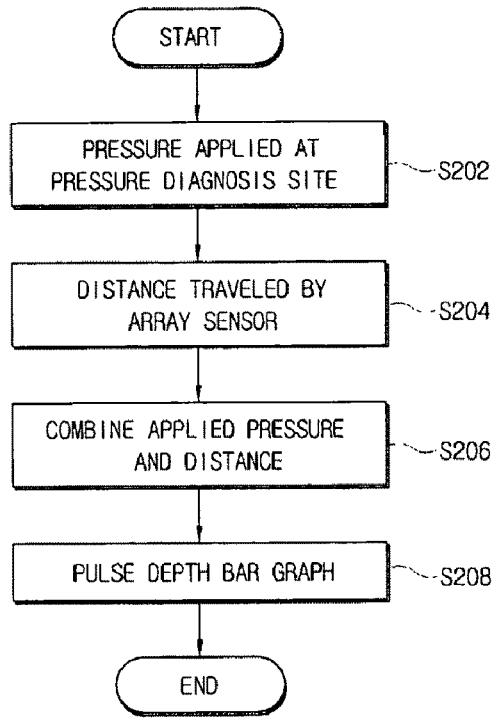
[Fig. 6]
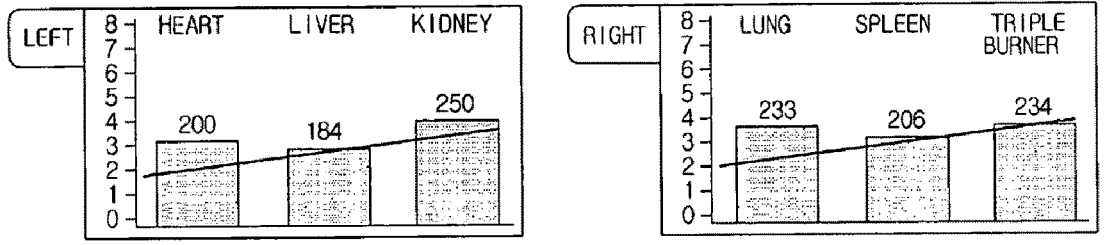
[Fig. 7]
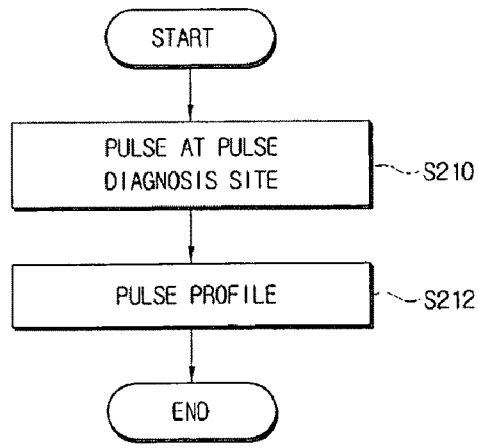

[Fig. 8]
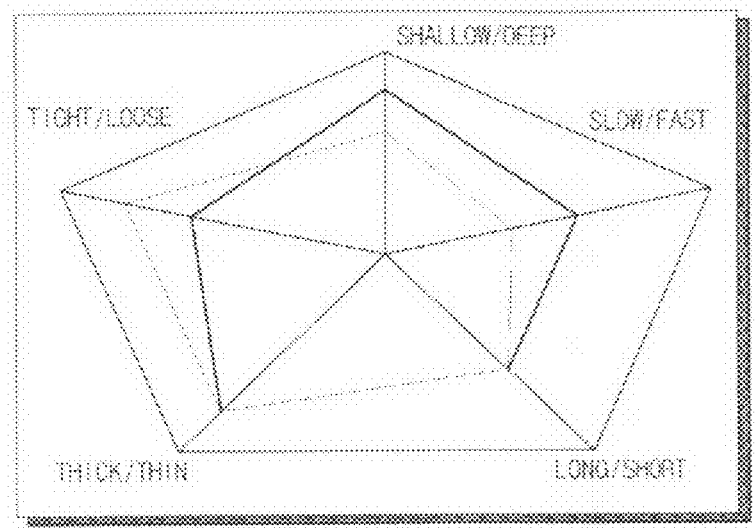
[Fig. 9]
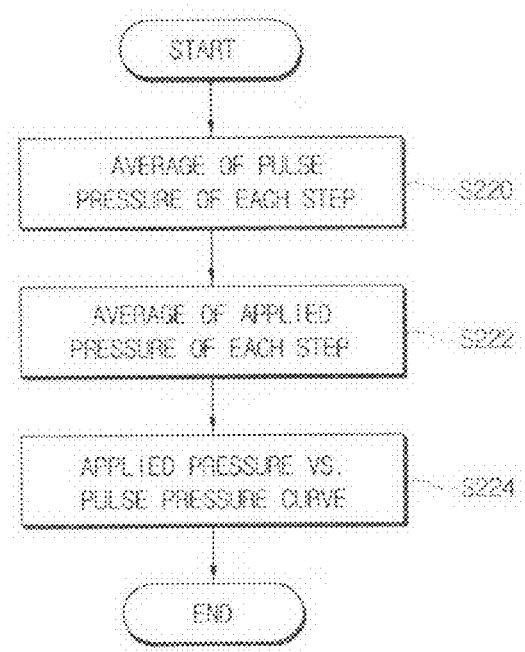
[Fig. 10]
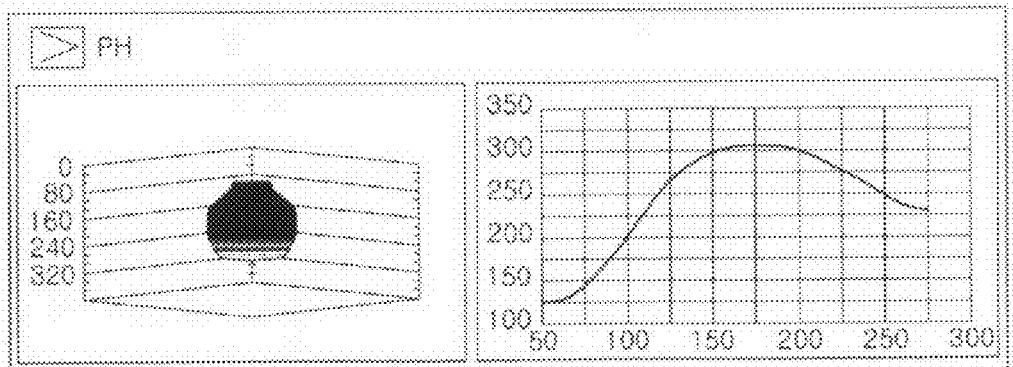

[Fig. 11]
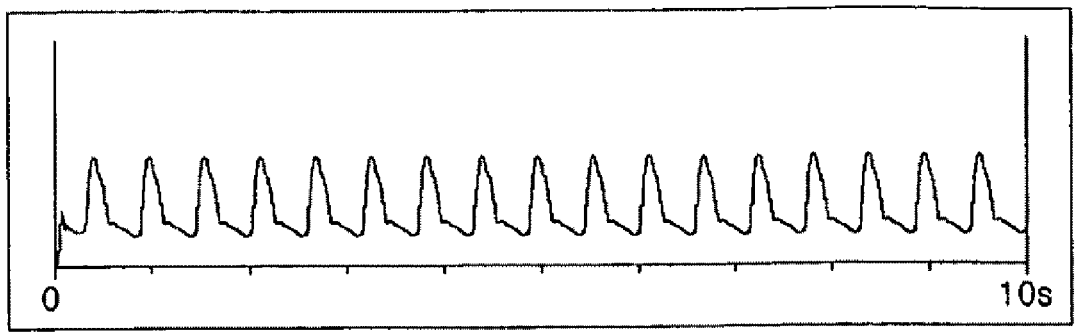
[Fig. 12]
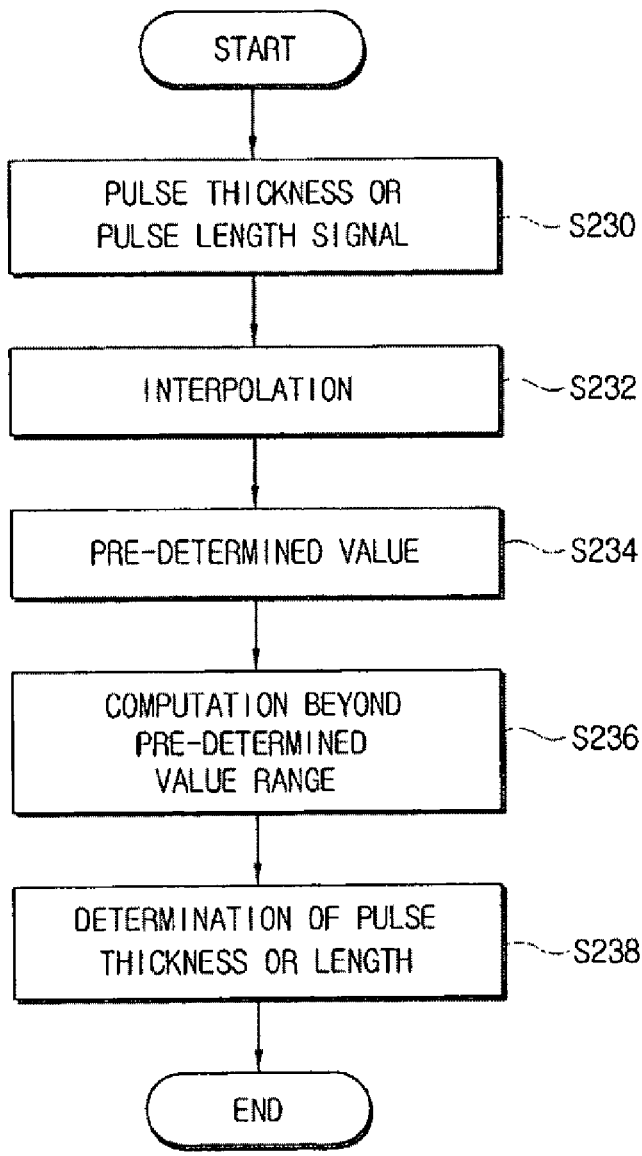

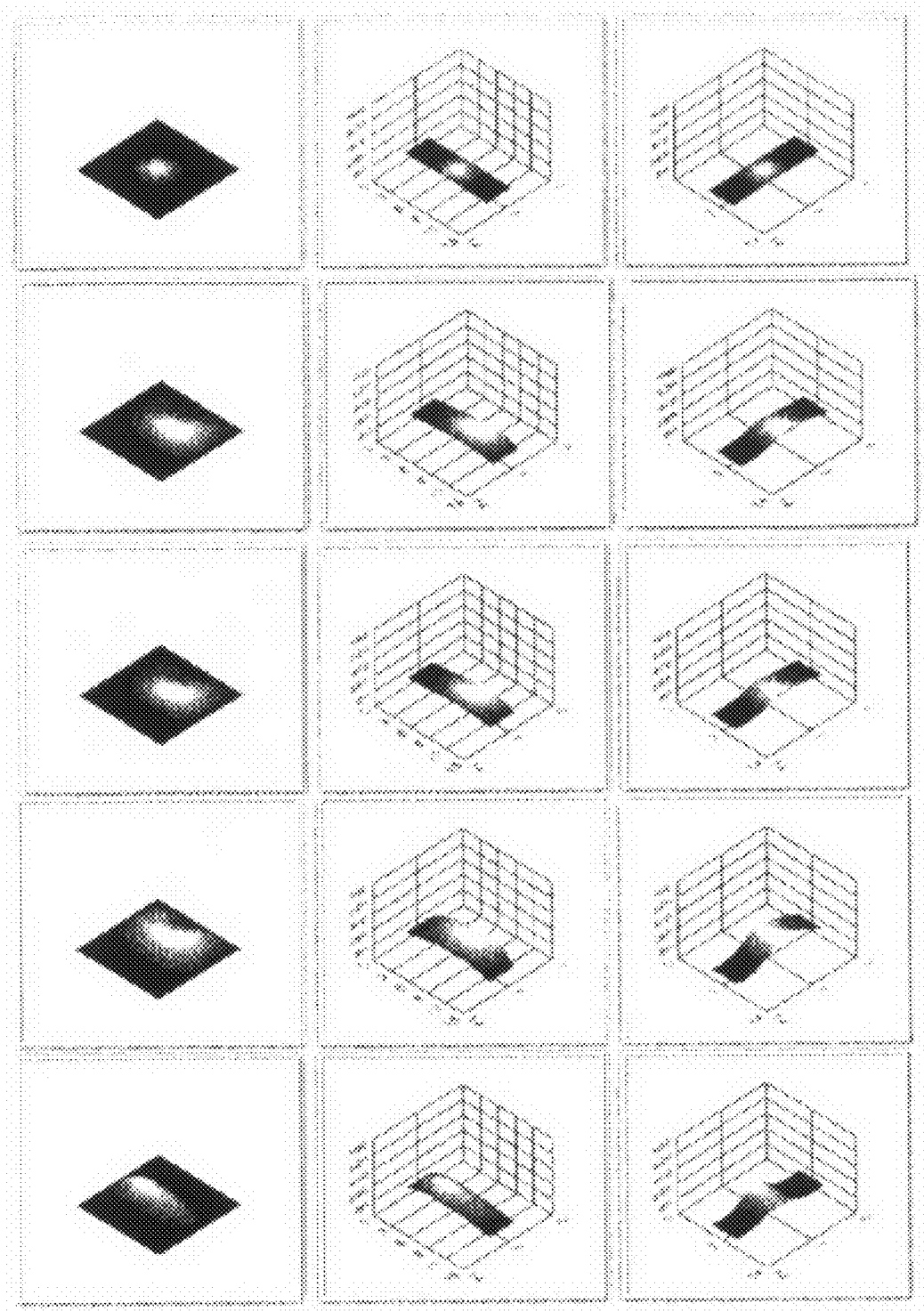
[Fig. 13]

APPARATUS FOR ANALYSING PULSE USING ARRAY OF PRESSURE SENSORS

The present application claims priority to PCT Patent Application No. PCT/KR2006/002396 (filed Jun. 21, 2006), which is hereby incorporated by reference in its entirety.

TECHNICAL FIELD

The present invention relates to an apparatus for analyzing pulse using an array of pressure sensors, more particularly to an apparatus for analyzing pulse using an array of pressure sensors that can be applied in medical field, including pulse diagnosis or blood vessel diagnosis in the Oriental medicine.

BACKGROUND ART

In general, diagnosis in the Oriental medicine is made in four categories—interviewing, listening, viewing and feeling pulse, a pulse diagnosis of judging the state of a patient by sensing the pulse of blood vessel. In the pulse diagnosis, such pulse characteristics as pulse intensity, pulse depth, pulse rate and pulse roughness are important. In order to measure the various pulse characteristics, the technique of exactly positioning blood vessels and accurately sensing the pulse is required.

In the six-site pulse diagnosis, which is one of commonly utilized pulse diagnosis techniques, the examiner places his/her three fingers (index finger, middle finger and ring finger), or each finger in sequence, on the three sites of the patient's wrist called "Chon", "Kwan" and "Chuck" in order to measure the pulse. The middle finger is placed on the "Kwan", or the coronary process on the radial artery, the index finger is placed on the "Chon", about 1-1.3 cm toward the palm, and the ring finger is placed on the "Chuck", about 1-1.3 cm toward the elbow. The examiner senses the pulse, applying a little force to the blood vessel. The pulse depth sensed by applying the force can be classified into "shallow", "moderate" and "deep". "Shallow" means that the pulse is clearest when a little force is applied. "Moderate" means that the pulse is clearest when the blood vessel is pressed more hardly. And, "deep" means that the pulse is clearest when the blood vessel is pressed the most hardly.

When checking the condition of the patient by pulse diagnosis, the examiner places his/her three fingers on "Chon", "Kwan" and "Chuck" and senses the pulse while pressing the blood vessel with different forces.

But, because each individual has different standard for the sensing and pulse intensity, the judgment of the patient's condition may be different from one examiner to another and thus is less reliable, if it is solely left to the examiner's subject sensing and experience. Accordingly, a lot of researches are being conducted recently, including one on a method for analyzing pulse that enables object and visual confirmation of the patient's pulse.

However, conventional methods for analyzing pulse are restricted in that a variety of pulse diagnosis techniques depending on the site of examination and the patient's constitution cannot be applied due to inability to exactly measure the pressure. And, the collected pulse data cannot be fully utilized.

DISCLOSURE OF INVENTION

Technical Problem

It is an object of the present invention to provide an apparatus for analyzing pulse using an improved array of pressure sensors that enables simultaneous measurement of applied pressure and pulse pressure using piezoresistive pressure sensors.

It is another object of the present invention to provide an apparatus for analyzing pulse using an array of pressure sensors that interpolates the signals collected by the array of pressure sensors to compute the length, thickness, etc. of the pulse and displays the result in four dimensions.

Technical Solution

To attain the objects, the present invention provides an apparatus for analyzing pulse using an array of pressure sensors comprising: an array of pressure sensors that measures the pulse data with a plurality of piezoresistive pressure sensors measuring the pressure applied to a pulse diagnosis site and the pulse pressure there; a moving part that moves the array of pressure sensors; a controller that controls the moving part, so that the array of pressure sensors can be positioned at the pulse diagnosis site, and analyzes the pulse data measured by the array of pressure sensors; and a display that displays the pulse profile analyzed by the controller.

Preferably, the controller controls the moving part so that the array of pressure sensors is positioned at a first position deemed to be the pulse diagnosis site and a predetermined pressure is applied there, stores the first position and the first pulse pressure measured there, controls the moving part so that the array of pressure sensors is positioned at a second first position neighboring the first position and a predetermined pressure is applied there, stores the second position and the second pulse pressure measured there and compares the first pulse pressure and the second pulse pressure. If the first pulse pressure is greater than the second pulse pressure, the controller controls the moving part so that the array of pressure sensors is positioned at the first position. Otherwise, if the second pulse pressure is greater, the controller controls the moving part so that the array of pressure sensors is positioned at the second position.

From the pressure applied at the pulse.diagnosis site and the distance traveled by the array of pressure sensors, the controller computes the coefficient of skin elasticity defined by the following formula:

$$E = \frac{p}{l}.$$

where E is the coefficient of skin elasticity, p is the pressure applied at the pulse diagnosis site and l is the distance traveled by the array of pressure sensors.

Also, the controller may compute the pulse depth by analyzing the pressure applied at the pulse diagnosis site.

Also, preferably, the controller computes pulse pressures at different pressures applied at the pulse diagnosis site along with other pulse data.

And, the pulse data may include at least one of pulse thickness and pulse length obtained from interpolation of the signals measured by the piezoresistive pressure sensors.

And, preferably, the display displays the pulse data in a three-dimensional space with x, y and z coordinates at various applied pressures or various times.

Advantageous Effects

As apparent from the above description, the apparatus for analyzing pulse using an array of pressure sensors in accordance with the present invention offers the following advantages.

First, since applied pressure and pulse pressure can be measured simultaneously using piezoresistive pressure sensors, various pulse diagnosis techniques can be applied and comparison and contrast with different techniques and different factors can be made easily.

Second, since pulse length, pulse thickness, etc. are computed and displayed in four dimensions from the interpolation of the signals collected from the array of pressure sensors, softness or roughness of the pulse and other pulse information can be conveyed visually.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

BRIEF DESCRIPTION OF THE DRAWINGS

The above and other objects, features and advantages of the present invention will become apparent from the following description of preferred embodiments given in conjunction with the accompanying drawings, in which:

FIG. 1 is a perspective view of an apparatus for analyzing pulse using an array of pressure sensors in accordance with an embodiment of the present invention.

FIG. 2 is a flowchart for the process in which the array of pressure sensors shown in FIG. 1 is moved to the pulse diagnosis site.

FIG. 3 shows the hand of a patient for illustrating the process of FIG. 2.

FIG. 4 is a flowchart for the process of computing the coefficient of skin elasticity.

FIG. 5 is a flowchart for the process of computing the pulse depth.

FIG. 6 shows the pulse depth data provided by the process of FIG. 5.

FIG. 7 is a flowchart for the process of computing the pulse profile data.

FIG. 8 shows the pulse profile data provided by the process of FIG. 7.

FIG. 9 is a flowchart for the process of providing the applied pressure vs. pulse pressure graph.

FIG. 10 shows the applied pressure vs. pulse pressure graph provided by the process of FIG. 9.

FIG. 11 shows the pulse vs. time graph provided by the process of FIG. 9.

FIG. 12 is a flowchart for the process of providing the four-dimensional pulse data.

FIG. 13 shows the four-dimensional pulse data provided by the process of FIG. 12.

BEST MODE FOR CARRYING OUT THE INVENTION

Although a few exemplary embodiments of the present invention have been shown and described, it will be appreciated by those skilled in the art that changes may be made in the embodiments without departing from the spirit of the invention, the scope of which is defined in the appended claims and their equivalents.

FIG. 1 is a perspective view of an apparatus for analyzing pulse using an array of pressure sensors in accordance with an embodiment of the present invention. Referring to the figure, the apparatus for analyzing pulse using an array of pressure sensors (100) in accordance with the present invention comprises an array of pressure sensors (110), a moving part (120), a controller (130) and a display (140).

The array of pressure sensors (110) may comprise a plurality of pressure sensors, which are preferably piezoresistive pressure sensors, that measure the applied pressure and the pulse pressure at the pulse diagnosis site. The applied pressure refers to the pressure applied at the pulse diagnosis site. Number and area of the pressure sensors may be adequately changed depending on the particular site to be diagnosed and the size of the particular artery.

The piezoresistive pressure sensor may comprise a diaphragm that converts the external pressure into stress and a portion that converts the vibration generated at the diaphragm into an electrical signal, so that the applied pressure and the corresponding pulse pressure can be measured simultaneously. The piezoresistive pressure sensor is preferably selected, so that the applied pressure and the pulse pressure can be measured within a linear range.

The conventional pulse diagnosis methods could not accurately measure the applied pressure, which is an important factor for analyzing the pulse. In contrast, the apparatus for analyzing pulse using an array of pressure sensors in accordance with the present invention enables accurate measuring of the applied pressure using piezoresistive pressure sensors.

Accordingly, a variety of pulse diagnosis techniques depending on the site of examination and the patient's constitution can be applied. And, the shallow/deep, slow/fast, vague/clear and long/short factors can be identified and the balance of the individual organs of lung, heart, spleen, liver and kidney can be compared. Also, the patient's constitution can be easily determined.

The array of pressure sensors (110) is fixed at one end of the moving part (120) and moves as the moving part (120) moves. Preferably, the moving part (120) is equipped with a plurality of joints, so that the array of pressure sensors (110) can move in three dimensions.

The controller (130) controls the moving part (120) so that the array of pressure sensors (110) can be positioned at the pulse diagnosis site and analyzes the pulse data measured by the array of pressure sensors (110).

The pulse diagnosis site may be searched by applying a constant pressure until the pressure sensor at the center of the array of sensors (110) receives the highest and clearest signal, while changing positions. A more detailed description will be given referring to FIG. 2.

First, the array of pressure sensors (110) is positioned at a first position deemed to be the pulse diagnosis site (S102) and the array of pressure sensors (110) is moved downward to apply pressure at the first position. The movement of the array of pressure sensors (110) is stopped if the applied pressure exceeds a pre-determined value and the applied pressure (Max_1), or the pulse pressure, and the first position are stored (S104).

Next, the array of pressure sensors (110) is moved to a second position neighboring the first position (S106) and is moved downward to apply pressure at the second position. The movement of the array of pressure sensors (110) is stopped if the applied pressure exceeds a pre-determined value and the applied pressure (Max_2), or the pulse pressure, and the second position are stored (S108).

Subsequently, the first pulse pressure and the second pulse pressure are compared (S110). If the first pulse pressure is larger, the array of pressure sensors (110) is positioned at the first position (S112). If the second pulse pressure is larger, the array of pressure sensors (110) is positioned at the second position (S114). This pulse diagnosis site search process may comprise a block (Process_n) that starts and proceeds an action when called and returns the result (S120).

The search for the pulse diagnosis site may be extended to more than 2 positions, for example to 4 neighboring positions. The method of determining the pulse diagnosis site by comparing the pulse pressures at four positions will be described referring to FIG. 3.

First, the array of pressure sensors (110) is moved to the position 1 and the pulse pressure and the position are stored. Then, the array of pressure sensors (110) is moved to the position 2 and the pulse pressure and the position are stored. If the pulse pressure at the position 1 is larger, the array of pressure sensors (110) is moved to the position 3', which is neighboring the position 1. Otherwise, if the pulse pressure at the position 2 is larger, the array of pressure sensors (110) is moved to the position 3", which is neighboring the position 2.

The applied pressure at the positions 1 and 3' and at the positions 2 and 3" are compared in the similar manner and the array of pressure sensors (110) is moved to the position at which the pulse pressure is larger.

The moving part (120) that moves the array of pressure sensors (10) to the pulse diagnosis site may be a device that is put on the patient's wrist with a small motor or a robot that enables diagnosis as the patient sits or lies.

Those skilled in the art will appreciate that the moving part (120) that moves the array of pressure sensors (110) to the pulse diagnosis site may be modified variously without departing from the spirit and scope of the present invention.

Preferably, the controller (130) computes the coefficient of skin elasticity. FIG. 4 is a flowchart for the process of computing the coefficient of skin elasticity.

Referring to FIG. 4, the computation of the coefficient of skin elasticity (S130 to S139) is carried out by measuring the pressure applied at the pulse diagnosis site and the distance traveled by the array of pressure sensors (110).

Preferably, the coefficient of skin elasticity is defined by the following formula:

$$E = \frac{p}{l}$$

where E is the coefficient of skin elasticity, p is the pressure applied at the pulse diagnosis site and l is the distance traveled by the array of pressure sensors (110).

The process of computing the coefficient of skin elasticity may comprise a step of checking if the value of the applied pressure lies in the error range (not shown in the figure).

The computed coefficient of skin elasticity is patient-specific and may be used to determine the patient's constitution or to judge the patient's skin condition by comparison with later measurement.

Preferably, the controller (130) analyzes the pulse data measured by the array of pressure sensors (110) and the display (140) displays the pulse data analysis result. Preferably, the pulse data contains pulse rate (slow or fast), pulse intensity (strong or weak), pulse thickness (thick or thin), pulse length (long or short), pulse shape (smooth or rough) and size of the applied pressure (shallow or deep).

The process of pulse analysis may comprise the step of providing the pulse depth (S202 to S208), providing the pulse data (S210, S212), providing the applied pressure vs. pulse pressure curve (S220 to S224) and providing the four-dimensional pulse data (S230 to S238). Here, the four-dimensional pulse data means that the pulse data is displayed in a 3-dimensional space with x, y and z coordinates at different times or different applied pressures. For example, the x coordinate may represent pulse length, the y coordinate may represent pulse thickness and the z coordinate may represent pulse pressure.

The process of analyzing the pulse data and the pulse data analysis result displayed by the display (140) will be described in more detail referring to FIG. 5 to FIG. 12.

Referring to FIG. 5, the process of providing the pulse depth (S202 to S208) may comprise the following steps. The pressure applied at the pulse diagnosis site measured by the array of pressure sensors (110) is collected (S202) and the distance traveled by the array of pressure sensors (110) is collected (S204). Then, the applied pressure and the distance traveled by the array of pressure sensors (110) are combined (S206) to obtain a bar graph (S208).

FIG. 6 shows the pulse depth data provided by the process of FIG. 5.

Referring to the figure, each bar in the bar graph represents the pulse depth for each organ and each line is the base line for the pulse depth. Judging from the base line, the hearth and lung pulses have large depth values, which implies that the pulse is deeper around the Chon than around the Kwan. According to the traditional pulse diagnosis theory, there is an illness at the corresponding site. As such, the examiner can find out an illness using the graphic data.

Now, referring to FIG. 7, the process of providing the pulse profile data is described (S210, S212).

Referring to the figure, the process of providing the pulse profile data (S210, 5212) may comprise the steps of collecting the pulse at the pulse diagnosis site measured by the array of pressure sensors (110) (S210) and creating a pulse profile graph (S212).

FIG. 8 shows the pulse profile data provided by the process of FIG. 7.

As shown in the figure, the pulse profile data provides such pulse profile information as shallow/deep, slow/fast, tight/loose, thick/thin and long/short.

Shallow/deep gives information about the pulse depth and slow/fast gives information about the pulse rate.

And, tight/loose gives information about the pulse tightness and thick/thin gives information about the pulse thickness.

Lastly, long/short gives information about the pulse length.

The thick pentagonal line lying about the center is the standard line for each organ and the thin pentagonal line lying slightly below is the line showing the state of the patient.

To take shallow/deep information for example, if the line lies out of the standard line, the patient has a shallow pulse. Otherwise, if it lies inside of the standard line, the patient has a deep pulse. The standard line and the measurement line are not restricted to pentagonal shapes. Depending on the pulse profile types to be measured, they may have such polygonal shapes as triangle, hexagon, etc. or prismoidal shapes.

Now, referring to FIG. 9, the process of providing the applied pressure vs. pulse pressure data (S220 to S224) is described. Referring to the figure, the process of providing the applied pressure vs. pulse pressure data (S220 to S224) may comprise the steps of calculating the average of the pulse pressure and the applied pressure measured by the array of pressure sensors (S220, S222) and creating an applied pressure vs. pulse pressure curve (S224).

FIG. 10 shows an example of the applied pressure vs. pulse pressure graph provided by the process of FIG. 9.

The graph on the left side is a three-dimensional one showing the change of the pulse pressure at various applied pressures. The ordinate represents the size of the applied pressure and the abscissa represents the size of the pulse pressure. The graph on the right side is a two-dimensional one showing the change of the pulse pressure at various applied pressures. The abscissa represents the size of the applied pressure and the ordinate represents the size of the pulse pressure.

The examiner can check the soundness and aging of the blood vessel using the applied pressure vs. pulse pressure graph. And, using a pulse vs. time graph as in FIG. 11, uniformess of pulse, presence of arrhythmia, etc. may be determined.

Since the period of illness, interrelationship of illnesses, illness of each organ, etc. cannot be found out by a single pulse, the applied pressure vs. pulse pressure graph will make a useful tool.

Lastly, referring to FIG. 12, the process of providing the four-dimensional pulse data is described. Referring to the figure, in the process of providing the four-dimensional pulse data (S230 to S238), each pulse data such as pulse thickness or pulse length is collected from each piezoresistive pressure sensor (S230). The collected pulse data signals are linked to each other by interpolation (S232). Preferably, the interpolation is carried out in a range wider than the pre-determined value range (S234, S236). The value may be selected adequately depending on the density of the piezoresistive sensors comprising the array of pressure sensors (110). By this process, such pulse data as pulse thickness, pulse length, etc. is obtained (S238).

FIG. 13 shows the pulse length and pulse thickness data as examples of the four-dimensional pulse data. The first graphic data is the pulse wave corresponding to the area of the array of pressure sensors. The second and third graph data are pulse length and pulse thickness data, respectively.

The pulse length can be computed by linking the signals of the sensors lying across the blood vessel by interpolation. And, the pulse thickness can be computed by linking the signals of the sensors lying along the blood vessel by interpolation.

During the pulse diagnosis, the sense of touch conveyed at the fingertips is very complicated: including smoothness or roughness of the pulse, flow of the pulse, tightness of the pulse, etc. It is difficult to quantify such sense with the conventional methods.

In contrast, since the present invention provides such pulse data as pulse length and pulse thickness in a three-dimensional space at various times or various applied pressures, pulse diagnosis information can be visually embodied.

Also, in the pulse analysis process (S200), using the pulse area (xy-plane), the size of the pulse pressure (z-axis) and the modulus of elasticity determined in the step S130 to 139, the thickness of the blood vessel, the ductility of the blood vessel and the thickness between the blood vessel and the skin can be found out.

Thus, the present invention enables determination of each patient's skin characteristics and the thickness between the blood vessel and the skin, which is an important factor in analyzing a shallow-deep pulse.

The invention claimed is:

1. An apparatus for analyzing a pulse using an array of pressure sensors comprising:

an array of pressure sensors including a plurality of piezoresistive pressure sensors that measure pulse data by measuring the pressure applied to a pulse diagnosis site and a pulse pressure there;

a moving part that moves the array of pressure sensors;

a controller that controls the moving part by positioning the array of pressure sensors at the pulse diagnosis site, and analyzes the pulse data measured by the array of pressure sensors to produce a pulse profile; and a display that displays the pulse profile produced by the controller, wherein the controller controls the moving part so that the array of pressure sensors is positioned at a first position deemed to be the pulse diagnosis site, applies a predetermined pressure at the first position, stores the first position and the first pulse pressure measured at the first position, controls the moving part so that the array of pressure sensors is positioned at a second position neighboring the first position, applies a predetermined pressure at the second position, stores the second position and the second pulse pressure measured at the second position, compares the first pulse pressure and the second pulse pressure and, if the first pulse pressure is greater than the second pulse pressure, the controller controls the moving part so that the array of pressure sensors is positioned at the first position, and if the second pulse pressure is greater than the first pulse pressure, the controller controls the moving part so that the array of pressure sensors is positioned at the second position.

2. The apparatus for analyzing a pulse using an array of pressure sensors as set forth in claim 1, wherein the controller computes the coefficient of skin elasticity defined by the following formula:

$$E = \frac{p}{l}$$

where E is a coefficient of skin elasticity, p is a pressure applied at a pulse diagnosis site and l is a distance traveled by the array of pressure sensors.

3. The apparatus for analyzing a pulse using an array of pressure sensors as set forth in claim 1, wherein the controller computes a pulse depth by analyzing the pressure applied at the pulse diagnosis site.

4. The apparatus for analyzing a pulse using an array of pressure sensors as set forth in claim 1, wherein the controller computes pulse pressures at different applied pressures at the pulse diagnosis site.

5. The apparatus for analyzing a pulse using an array of pressure sensors as set forth in claim 1, wherein the pulse data includes at least one of a pulse thickness and a pulse length obtained from interpolation of the signals measured by the piezoresistive pressure sensors.

6. The apparatus for analyzing a pulse using an array of pressure sensors as set forth in claim 5, wherein the pulse data is displayed in a three-dimensional space with x, y and z coordinates representing varied applied pressures and varied times.

* * * * *